United States Patent
Miyazaki et al.

(10) Patent No.: US 11,944,620 B2
(45) Date of Patent: *Apr. 2, 2024

(54) STABLE PHARMACEUTICAL COMPOSITION FOR ORAL ADMINISTRATION

(71) Applicant: ASTELLAS PHARMA INC., Tokyo (JP)

(72) Inventors: Masakazu Miyazaki, Tokyo (JP); Ryohei Ishiba, Tokyo (JP); Yuki Takaishi, Tokyo (JP); Fumiaki Uejo, Tokyo (JP)

(73) Assignee: ASTELLAS PHARMA INC., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/316,368

(22) Filed: May 12, 2023

(65) Prior Publication Data

US 2023/0277530 A1    Sep. 7, 2023

Related U.S. Application Data

(63) Continuation of application No. 18/085,842, filed on Dec. 21, 2022, which is a continuation of application No. 17/000,763, filed on Aug. 24, 2020, now abandoned, which is a continuation of application No. 15/741,377, filed as application No. PCT/JP2016/069615 on Jul. 1, 2016, now Pat. No. 10,786,500.

(30) Foreign Application Priority Data

Jul. 3, 2015  (JP) ................. 2015-134817

(51) Int. Cl.
| | |
|---|---|
| *A61K 31/497* | (2006.01) |
| *A61K 9/20* | (2006.01) |
| *A61K 47/10* | (2017.01) |
| *A61K 47/26* | (2006.01) |

(52) U.S. Cl.
CPC .............. *A61K 31/497* (2013.01); *A61K 9/20* (2013.01); *A61K 9/2095* (2013.01); *A61K 47/10* (2013.01); *A61K 47/26* (2013.01)

(58) Field of Classification Search
CPC ......... A61K 31/497; A61K 9/20; A61K 47/10
USPC ...................................... 514/252.1
See application file for complete search history.

(56) References Cited

U.S. PATENT DOCUMENTS

| | | | |
|---|---|---|---|
| 8,969,336 B2 | 3/2015 | Shimada et al. | |
| 9,775,832 B2 | 10/2017 | Kojima et al. | |
| 10,786,500 B2 * | 9/2020 | Miyazaki | .............. A61K 9/20 |
| 11,045,468 B2 | 6/2021 | Eguchi et al. | |
| 2010/0278930 A1 * | 11/2010 | Okumura | ........... A61K 31/4422 977/773 |
| 2012/0040968 A1 | 2/2012 | Shimada et al. | |
| 2013/0273161 A1 | 10/2013 | Bouillot et al. | |
| 2014/0371196 A1 * | 12/2014 | Shimada | .............. C07D 241/26 514/255.06 |
| 2016/0339020 A1 | 11/2016 | Eguchi et al. | |
| 2021/0290618 A1 | 9/2021 | Eguchi et al. | |
| 2023/0129146 A1 | 4/2023 | Miyazaki et al. | |

FOREIGN PATENT DOCUMENTS

| | | |
|---|---|---|
| CN | 102421761 A | 4/2012 |
| CN | 103458877 A | 12/2013 |
| EP | 2428508 A1 | 3/2012 |
| JP | 2014-501770 A | 1/2014 |
| KR | 10-2012-0007523 A | 1/2012 |
| RU | 2526253 | 8/2014 |
| WO | 2010/128659 A1 | 11/2010 |
| WO | 2012/093161 A1 | 7/2012 |
| WO | 2015/119122 A1 | 8/2015 |

OTHER PUBLICATIONS

Nakai, Yoshinobu, "Relationship between Powder Characteristics and the Pharmaceutical Preparations," (and English Translation), J. Society of Powder Technology (1988), vol. 25 (6), pp. 388-394 and pp. 1-17. (Year: 1988).*
Copending U.S. Appl. No. 18/316,364, commonly assigned, filed May 12, 2023. (Year: 2023).*
Copending U.S. Appl. No. 18/316,368, commonly assigned, filed May 12, 2023. (Year: 2023).*
Copending U.S. Appl. No. 18/316,370, commonly assigned, filed May 12, 2023. (Year: 2023).*
Copending U.S. Appl. No. 18/316,373, commonly assigned, filed May 12, 2023. (Year: 2023).*
Non-final Office Action in U.S. Appl. No. 17/327,337 (dated Apr. 2023).

(Continued)

*Primary Examiner* — Craig D Ricci
*Assistant Examiner* — Janet L Coppins
(74) *Attorney, Agent, or Firm* — Venable LLP

(57) ABSTRACT

Provided is a stable pharmaceutical composition for oral administration comprising 6-ethyl-3-({3-methoxy-4-[4-(4-methylpiperazin-1-yl)piperidin-1-yl]phenyl}amino)-5-(tetrahydro-2H-pyran-4-ylamino)pyrazine-2-carboxamide (hereinafter referred to as compound A) or a pharmaceutically acceptable salt thereof, wherein the generation of related substances during storage is inhibited. In the stable pharmaceutical composition for oral administration, the proportion of crystals of compound A or a pharmaceutically acceptable salt thereof is 60% or more with respect to the total amount of compound A or a pharmaceutically acceptable salt thereof.

18 Claims, No Drawings

(56) References Cited

OTHER PUBLICATIONS

Extended European Search Report in European Application No. 23150843.3 (dated Jul. 2023).
First Office Action in Chinese Application No. 201680039513.0 (dated Mar. 20, 2020).
L.Y. Galichet, "Cellulose, Microcrystalline," in Handbook of Pharmaceutical Excipients, 5th ed. (Raymond C. Rowe et al., eds.), pp. 132-135 (2006).
S. Edge et al., "Lactose, Anhydrous," in Handbook of Pharmaceutical Excipients, 5th ed. (Raymond C. Rowe et al., eds.), pp. 385-388 (2006).
S. Edge et al., "Lactose, Monohydrate," in Handbook of Pharmaceutical Excipients, 5th ed. (Raymond C. Rowe et al., eds.), pp. 389-395 (2006).
N.A. Armstrong, "Mannitol," in Handbook of Pharmaceutical Excipients, 5th ed. (Raymond C. Rowe et al., eds.), pp. 449-453 (2006).
M.C. Gohel, "A Review of Co-Processed Directly Compressible Excipients," 8(1) J. Pharm. Pharmaceut Sci 76-93 (Apr. 2005).
Office Action with Search Report in Russian Application No. 2018103354/04 (dated Nov. 28, 2019).
First Office Action in Mexican Application No. MX/a/2017/016862 (dated Feb. 28, 2020).
First Office Action in Indonesian Application No. P00201800751 (dated Apr. 6, 2020).
Communication Pursuant to Article 94(3) EPC in European Application No. 16 821 324.7 (dated Dec. 12, 2019).
Notice of Reasons for Rejection in Japanese Application No. 2017-077939 (dated May 12, 2020).
First Substantive Examination Report in Philippine Application No. Jan. 2017/502252 (dated Jul. 9, 2020).
Y. Nakai, "Relationship Between Powder Characteristics and the Pharmaceutical Preparations," 25(6) Journal of the Society of Powder Technology 388-394 (1988).
International Search Report in International Application No. PCT/JP2016/069615 (dated Aug. 16, 2016).
International Preliminary Report on Patentability in International Application No. PCT/JP2016/069615 (dated Jan. 9, 2018).
Extended European Search Report in European Application No. 16821324. 7 (dated Jan. 25, 2019).
First Office Action in Thai Patent Application No. 1701007888 PCT (dated Jan. 22, 2019).
Second Office Action in Chinese Application No. 201680039513.0 (dated Dec. 11, 2020).
Office Action in Taiwanese Application No. 105121008 (dated Sep. 25, 2020).
H. Leonhard Ohrem et al., "Why is Mannitol Becoming More and More Popular as a Pharmaceutical Excipient in Solid Dosage Forms?" Pharm. Dev. Technol., Early Online: 1-6 (2013).
ICH Guideline Q1A(R2), "Stability Testing of New Drug Substances and Products", pp. 1-18 (Feb. 2003).
ICH Topic Q3B(R2), "Impurities In New Drug Products" (EMA), pp. 1-14 (Jun. 2006).
Decision of Rejection in Taiwanese Application No. 105121008 (dated Jan. 2021).
Notice of the Result of Substantive Examination in Indonesian Application No. P00201800751 (dated Jan. 2021).
Subsequent Substantive Examination Report in Philippine Application No. 1/2017/502252 (dated Jan. 2021).
Somnath Singh et al., "Effect of Polyols on the Conformational Stability and Biological Activity of a Model Protein Lysozyme," 4(3) Art. 42 AAPS PharmSciTech 1-9 (2003).
I.M. Pertzev et al. (eds), "Excipients and Their Use in Pharmacy" in Pharmaceutical and Biomedical Aspects of Drugs, vol. 1, Ch. 11, pp. 253-254 (1999).
S.Ya. Skachilova et al., "Drug Technology: Biopharmaceutical Aspects of Pharmacopeia Substances," 8 Pharmacia 29 (2012).
Office Action in Russian Application No. 2018103354 (dated Apr. 2021).

Office Action in Taiwanese (ROC) Reexamination Patent Application No. 105121008 (dated Aug. 2021).
Third Office Action in Indonesian Patent Application No. P00201800751 (dated Sep. 2021).
Examination Report in Vietnamese Patent Application No. 1-2018-00457 (dated Nov. 2021).
Office Action in Canadian Application No. 2,989,534 (dated May 2022).
Yihong Qiu et al. (eds), Developing Solid Oral Dosage Forms: Pharmaceutical Theory and Practice, pp. 1-943 (1st ed. 2009).
Sumie Yoshioka et al., Stability of Drugs and Dosage Forms, Ch. 2.2.11, pp. 107-108 (2002).
Notice of Preliminary Rejection in Korean Application No. 10-2012-0007523 (dated Sep. 2023).
Office Action in Vietnamese Application No. 1-2018-00457 (dated Sep. 2023).
Notice of Preliminary Rejection in Korean Application No. 10-2017-7037673 (dated Sep. 2023).
Notice of Opposition by Sandoz AG in European Patent No. 3 318 259 (dated Oct. 2023).
Notice of Opposition by Generics [UK] Limited in European Patent No. 3 318 259 (dated Oct. 2023).
Mark Gibson (ed.), "Pharmaceutical Preformulation and Formulation," 2nd ed., pp. 231-234 (2009).
Michael E. Aulton (ed.), "Pharmaceutics—The Science of Dosage Form Design," 2nd ed., pp. 379-386 (2002).
Geoff G.Z. Zhang et al., "Phase Transformation Considerations During Process Development and Manufacture of Solid Oral Dosage Forms," 56(3) Adv. Drug Deliv. Rev. 371-390 (Feb. 2004).
A. Pandey et al., "Pharmaceutical Preformulation Studies with Special Emphasis on Excipients Compatibility," 2(3) Int. J. Pharm. Technol. 1029-1048 (Jun. 2011).
Claes Ahlneck et al., "The Molecular Basis of Moisture Effects on the Physical and Chemical Stability of Drugs in the Solid State," 62(2-3) Int. J. Pharm. 87-95 (1990).
FDA Guidance for Industry: Q1A(R2) Stability Testing of New Drug Substances and Products, pp. 1-22 (Nov. 2003).
EMA Draft Guideline on the Chemistry of Active Substances, pp. 1-16 (Feb. 2015).
Decision T 0777/08 by the Boards of Appeal of the European Patent Office, pp. 1-17 (May 2011).
Stephen Byrn et al., "Pharmaceutical Solids: A Strategic Approach to Regulatory Considerations," 12(7) Pharm. Res. 945-954 (Jul. 1995).
Bruno C. Hancock et al., "Molecular Mobility of Amorphous Pharmaceutical Solids Below Their Glass Transition Temperatures," 12(6) Pharm. Res. 799-806 (Jun. 1995).
Rolf Hilfiker (ed.), "Polymorphism in the Pharmaceutical Industry," pp. 224-228 and 333-336 (2006).
Harry G. Brittain (ed.), "Polymorphism in Pharmaceutical Solids," pp. 338-343 (1999).
Norman Anthony Armstrong et al., "Tablet Manufacture" in "Encyclopedia of Pharmaceutical Technology," 3rd ed., pp. 3653-3672 (2007).
FDA Guidance for Industry: ANDAs: Pharmaceutical Solid Polymorphism, pp. 1-10 (Jul. 2007).
M. E. Aulton (ed.), "Pharmaceutics: The Science of Dosage Form Design," 2nd ed., pp. 114-115 and 128-130 (2002).
Leon Lachman et al. (eds.), "The Theory and Practice of Industrial Pharmacy," 2nd ed., pp. 503-504 (1976).
Anthony J. Hickey et al. (eds), "Pharmaceutical Process Engineering," pp. 86-87 (2001).
Arthur H. Kibbe (ed.), "Handbook of Pharmaceutical Excipients," 3rd ed., pp. 324-328 (2000).
Howard C. Ansel et al. et al., "Pharmaceutical Dosage Forms and Drug Delivery Systems," 5th ed., pp. 69-82, 134-195 (1990).
Larry L. Augsburger et al., "Tablet Formulation" in "Encyclopedia of Pharmaceutical Technology," 3rd ed., pp. 3641-3652 (2007).
Sisir Bhattacharya et al., "Local Mobility in Amorphous Pharmaceuticals—Characterization and Implications on Stability," 98(9) J. Pharm. Stud. 2935-2953 (Sep. 2009).

(56) References Cited

OTHER PUBLICATIONS

Shabbir S. Dawoodbhai, "Optimization and Use of Talc in Direct Compression Tablet Formulations," Open Access Dissertations, Paper 341, 307 pages (1989).

Shabbir S. Dawoodbhai, "Optimization of Tablet Formulations Containing Talc," 17 Drug Dev. Ind. Pharm. 1343-1371 (1991).

Bruno C. Hancock et al., "Characteristics and Significance of the Amorphous State in Pharmaceutical Systems," 86(1) J. Pharm. Sci. 1-12 (Jan. 1997).

Silke Klick et al., "Toward a Generic Approach for Stress Testing of Drug Substances and Drug Products," Pharmaceutical Testing, pp. 48-66 (Feb. 2005).

Hiroko Miura et al., "Effect of Size of Tablets on Easiness of Swallowing and Handling Among the Frail Elderly," 44 Nippon Ronen Igakkai Zasshi 627-633 (2007).

H. Leonhard Ohrem et al., "Why is Mannitol Becoming More and More Popular as a Pharmaceutical Excipient in Solid Dosage Forms?," 19(3) Pharm. Dev. Technol. 257-262 (Mar. 2013).

Yihong Qiu et al., "Developing Solid Oral Dosage Forms, Pharmaceutical Theory and Practice," (1st ed.), p. 414 (2009).

"Remington: The Science and Practice of Pharmacy," 19th ed., Alfonso R. Gennato (ed.), pp. 1447-1462, 1615-1649 (1995).

Raymond C. Rowe et al., "Handbook of Pharmaceutical Excipients," 5th ed., pp. 93-95, 102-104, 385-398, 449-453, 767-769 (2006).

Sumie Yoshioka et al., "Stability of Drugs and Dosage Forms," 1st ed., pp. 107-137, 139-203, 205-225, 227-268 (2002).

Herbert A. Lieberman et al., "Pharmaceutical Dosage Forms," vol. 1, 2nd ed., pp. 1-73, 96-101 (1989).

Report on the Filing or Determination of an Action Regarding a Patent or Trademark re U.S. Pat. No. 10,786,500: *Astellas Pharma Inc et al.* v. *Sandoz, Inc.* (Case 2:23-cv-01214-ES-JSA; filed Mar. 2023).

"Remington: The Science and Practice of Pharmacy," 20th ed., Alfonso R. Gennato (ed.), pp. 700-720, 858-893 (2000).

\* cited by examiner

STABLE PHARMACEUTICAL COMPOSITION FOR ORAL ADMINISTRATION

CROSS-REFERENCE TO RELATED APPLICATION

This application is a continuation application of U.S. patent application Ser. No. 18/085,842, filed Dec. 21, 2022, which is a continuation application of U.S. patent application Ser. No. 17/000,763, filed Aug. 24, 2020, now abandoned, which is a continuation application of U.S. patent application Ser. No. 15/741,377, which was the National Stage of International Application No. PCT/JP2016/069615, filed Jul. 1, 2016, now U.S. Pat. No. 10,786,500, and which are all incorporated herein by reference in their entirety and which claim the benefit of Japanese Patent Application No. 2015-134817, filed Jul. 3, 2015.

TECHNICAL FIELD

The present invention relates to a stable pharmaceutical composition for oral administration comprising 6-ethyl-3-({3-methoxy-4-[4-(4-methylpiperazin-1-yl)piperidin-1-yl]phenyl}amino)-5-(tetrahydro-2H-pyran-4-ylamino)pyrazine-2-carboxamide or a pharmaceutically acceptable salt thereof.

BACKGROUND ART

6-Ethyl-3-({3-methoxy-4-[4-(4-methylpiperazin-1-yl)piperidin-1-yl]phenyl}amino)-5-(tetrahydro-2H-pyran-4-ylamino)pyrazine-2-carboxamide (hereinafter referred to as compound A in some cases) is a compound represented by the following chemical structural formula. It has been reported that Compound A or a pharmaceutically acceptable salt thereof has, for example, an inhibitory activity of a kinase activity of an EML4 (Echinoderm microtubule associated protein like-4)-ALK (Anaplastic lymphoma kinase) fusion protein, and is useful as an active ingredient of a pharmaceutical composition for treating cancer (Patent literature 1).

[Chem. 1]

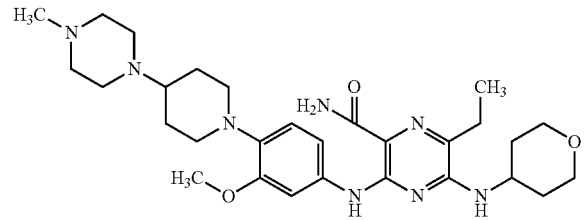

From the viewpoint of the safety of the patients, it is desirable that the generation of related substances is inhibited during storage of a formulation. For example, the Ministry of Health, Labor and Welfare in Japan published a specification of drug products, namely, the concept of related substances (impurities) in drug products as observed during stability tests (Pharmaceutical and Food Safety Bureau, Evaluation and Licensing Division Notification No. 0624001 "Revision of the Guideline on the Impurities in the Medicinal Products with New Active Ingredients"). According to the revised guideline, for example, when the amount of the drug substance to be administered per day is 10 mg to 100 mg, the threshold of related substances requiring safety qualification in a drug product is the lower of either 0.5% as the percentage of the related substances contained in the drug substance or 200 μg as the total daily intake of the related substances. Therefore, it is useful to provide a stable formulation comprising Compound A or a pharmaceutically acceptable salt thereof, in which the generation of related substances during storage is inhibited.

CITATION LIST

Patent Literature

[Patent literature 1] WO 2010/128659

SUMMARY OF INVENTION

Technical Problem

An object of the present invention is to provide a stable pharmaceutical composition for oral administration comprising Compound A or a pharmaceutically acceptable salt thereof, wherein the generation of related substances during storage is inhibited.

Solution to Problem

Compound A hemifumarate is stable in heat and humidity alone, and an increase in related substances was not observed under certain storage conditions, such as a severity test, or the like, of medicinal products. However, when the pharmaceutical composition of Comparative Example 1 described below was prepared, in accordance with an embodiment of a wet granulation method, a high shear granulation method, by granulating Compound A hemifumarate together with microcrystalline cellulose and the like, which did not cause a incompatibility with Compound A hemifumarate, using water, and drying the granulated product to make a formulation, it was found that related substances unexpectedly increased. In order to inhibit the generation of related substances of Compound A during storage, the inventors conducted intensive studies, and as a result, found that the generation of related substances of Compound A could be inhibited by inhibiting a decrease in the proportion of crystals of Compound A hemifumarate during the formulation step, and completed the present invention.

The present invention provides:

[1] a stable pharmaceutical composition for oral administration comprising 6-ethyl-3-({3-methoxy-4-[4-(4-methylpiperazin-1-yl)piperidin-1-yl]phenyl}amino)-5-(tetrahydro-2H-pyran-4-ylamino)pyrazine-2-carboxamide or a pharmaceutically acceptable salt thereof, wherein the proportion of crystals of 6-ethyl-3-({3-methoxy-4-[4-(4-methylpiperazin-1-yl)piperidin-1-yl]phenyl}amino)-5-(tetrahydro-2H-pyran-4-ylamino)pyrazine-2-carboxamide or a pharmaceutically acceptable salt thereof is 60% or more with respect to the total amount of 6-ethyl-3-({3-methoxy-4-[4-(4-methylpiperazin-1-yl)piperidin-1-yl]phenyl}amino)-5-(tetrahydro-2H-pyran-4-ylamino)pyrazine-2-carboxamide or a pharmaceutically acceptable salt thereof;

[2] the pharmaceutical composition for oral administration of [1], wherein the percentage of a related substance of 6-ethyl-3-({3-methoxy-4-[4-(4-methylpiperazin-1-yl)piperidin-1-yl]phenyl}amino)-5-(tetrahydro-2H-pyran-4-ylamino)pyrazine-2-carboxamide is 0.20% or less, after storage of the pharmaceutical composition for oral administration under opened conditions of 40° C. and 75% relative humidity for 1 month;

[3] the pharmaceutical composition for oral administration of [1] or [2], further comprising a pharmaceutical additive capable of controlling a water content in a formulation;

[4] the pharmaceutical composition for oral administration of [3], wherein the pharmaceutical additive capable of controlling a water content in a formulation is sugars and/or sugar alcohols;

[5] the pharmaceutical composition for oral administration of [4], wherein the sugars and/or sugar alcohols are lactose and/or D-mannitol;

[6] the pharmaceutical composition for oral administration of any one of [3] to [5], wherein the content of the pharmaceutical additive capable of controlling a water content in a formulation is 20% by weight to 90% by weight with respect to the total weight of the pharmaceutical composition for oral administration;

[7] a method of manufacturing a stable pharmaceutical composition for oral administration, said method comprising:
  (1) mixing 6-ethyl-3-({3-methoxy-4-[4-(4-methylpiperazin-1-yl)piperidin-1-yl]phenyl}amino)-5-(tetrahydro-2H-pyran-4-ylamino)pyrazine-2-carboxamide or a pharmaceutically acceptable salt thereof with a pharmaceutical additive capable of controlling a water content in a formulation,
  (2) granulating the mixture so that the proportion of crystals of 6-ethyl-3-({3-methoxy-4-[4-(4-methylpiperazin-1-yl)piperidin-1-yl]phenyl}amino)-5-(tetrahydro-2H-pyran-4-ylamino)pyrazine-2-carboxamide or a pharmaceutically acceptable salt thereof is 60% or more with respect to the total amount of 6-ethyl-3-({3-methoxy-4-[4-(4-methylpiperazin-1-yl)piperidin-1-yl]phenyl}amino)-5-(tetrahydro-2H-pyran-4-ylamino) pyrazine-2-carboxamide or a pharmaceutically acceptable salt thereof, and
  (3) compression-molding the granulated product;

[8] the method of manufacturing a pharmaceutical composition for oral administration of [7], wherein the granulation is carried out at a water content of the granulated product of 30% or less;

[9] the method of manufacturing a pharmaceutical composition for oral administration [7] or [8], wherein the pharmaceutical additive capable of controlling a water content in a formulation is sugars and/or sugar alcohols;

[10] a method of stabilizing 6-ethyl-3-({3-methoxy-4-[4-(4-methylpiperazin-1-yl)piperidin-1-yl]phenyl}amino)-5-(tetrahydro-2H-pyran-4-ylamino)pyrazine-2-carboxamide or a pharmaceutically acceptable salt thereof, in a stable pharmaceutical composition for oral administration comprising 6-ethyl-3-({3-methoxy-4-[4-(4-methylpiperazin-1-yl)piperidin-1-yl]phenyl}amino)-5-(tetrahydro-2H-pyran-4-ylamino)pyrazine-2-carboxamide or a pharmaceutically acceptable salt thereof, by setting the proportion of crystals of 6-ethyl-3-({3-methoxy-4-[4-(4-methylpiperazin-1-yl)piperidin-1-yl]phenyl}amino)-5-(tetrahydro-2H-pyran-4-ylamino)pyrazine-2-carboxamide or a pharmaceutically acceptable salt thereof with respect to the total amount of 6-ethyl-3-({3-methoxy-4-[4-(4-methylpiperazin-1-yl)piperidin-1-yl]phenyl}amino)-5-(tetrahydro-2H-pyran-4-ylamino)pyrazine-2-carboxamide or a pharmaceutically acceptable salt thereof to 60% or more, and/or by adding a pharmaceutical additive capable of controlling a water content in a formulation;

[11] use of a pharmaceutical additive capable of controlling a water content in a formulation in the manufacture of a stable pharmaceutical composition for oral administration comprising 6-ethyl-3-({3-methoxy-4-[4-(4-methylpiperazin-1-yl)piperidin-1-yl]phenyl}amino)-5-(tetrahydro-2H-pyran-4-ylamino)pyrazine-2-carboxamide or a pharmaceutically acceptable salt thereof;

[12] a stable pharmaceutical composition for oral administration comprising 6-ethyl-3-({3-methoxy-4-[4-(4-methylpiperazin-1-yl)piperidin-1-yl]phenyl}amino)-5-(tetrahydro-2H-pyran-4-ylamino)pyrazine-2-carboxamide or a pharmaceutically acceptable salt thereof, and lactose and/or D-mannitol; and

[13] a stable pharmaceutical composition for oral administration comprising 6-ethyl-3-({3-methoxy-4-[4-(4-methylpiperazin-1-yl)piperidin-1-yl]phenyl}amino)-5-(tetrahydro-2H-pyran-4-ylamino)pyrazine-2-carboxamide or a pharmaceutically acceptable salt thereof, and D-mannitol.

Advantageous Effects of Invention

According to the present invention, a stable pharmaceutical composition for oral administration comprising Compound A or a pharmaceutically acceptable salt thereof, wherein the generation of related substances during storage is inhibited, can be provided.

DESCRIPTION OF EMBODIMENTS

The term "stable" as used herein means to have stability against, for example, heat, light, temperature, and/or humidity. For example, after a pharmaceutical composition for oral administration is allowed to stand under the following conditions, it is defined as an embodiment in which related substances of Compound A contained in the pharmaceutical composition for oral administration is a specific percentage or less. For example, after a pharmaceutical composition for oral administration is allowed to stand at 70° C. for 9 days, at 40° C. and 75% relative humidity (hereinafter X % relative humidity is sometimes abbreviated as X % RH) for 6 months in an embodiment, at 40° C. and 75% RH for 3 months in an embodiment, at 40° C. and 75% RH for 1 month in an embodiment, at 25° C. and 60% RH for 12 months in an embodiment, at 25° C. and 60% RH for 6 months in an embodiment, at 25° C. and 60% RH for 3 months in an embodiment, and at 25° C. and 60% RH for 1 month in an embodiment, it is defined as the percentage of related substances of Compound A contained in the pharmaceutical composition for oral administration measured by a high-performance liquid chromatographic method (hereinafter sometimes abbreviated as an HPLC method) being, for example, 0.50% or less, 0.20% or less in an embodiment, and 0.10% or less in an embodiment. In an embodiment, after a pharmaceutical composition for oral administration is allowed to stand under opened conditions of 40° C. and 75% RH for 1 month, 3 months, or 6 months, it is defined as the percentage of related substances of Compound A contained in the pharmaceutical composition for oral administration measured by an HPLC method being, for example, 0.20% or less, and 0.10% or less in an embodiment.

The term "related substance of Compound A" is defined as, for example, an oxidative decomposition product of Compound A, and in an embodiment, a substance having a relative retention time of about 1.06 with respect to the peak of Compound A, as measured by the HPLC method described below. In connection with this, the related substance having a relative retention time of about 1.06 with respect to the peak of Compound A is presumed to be an oxidative decomposition product of Compound A. Numerical values used are interpreted as larger variable values, in general, within an experimental error (for example, within the 95% confidence interval for the mean), or within ±10% of the indicated value, and all the values of the variable.

The "proportion of crystals" of Compound A or a pharmaceutically acceptable salt thereof is defined as the proportion of crystals with respect to the total amount of Compound A or a pharmaceutically acceptable salt thereof, and can be calculated by near-infrared spectroscopy (NIR), as described below, or the like.

The term "loss on drying" as used herein means the amount of moisture that is contained in a sample and lost by drying. The loss on drying can be calculated, for example, by the following equation:

Loss on drying (%)=(weight (mass) reduced by drying/weight (mass) of a sample at the beginning of the measurement of loss on drying)×100

More particularly, the loss on drying can be calculated by the following equation:

Loss on drying (%)=[(weight (mass) of a sample at the beginning of the measurement of loss on drying−weight (mass) of a sample at the end of the measurement of loss on drying)/(weight (mass) of a sample at the beginning of the measurement of loss on drying)]×100

Compound A or a pharmaceutically acceptable salt thereof, which is used in the present invention, is easily available, for example, by a method described in Patent literature 1, or in a similar fashion to that.

Compound A may be in a free form, which does not form a salt, and may form a pharmaceutically acceptable salt with an acid. Examples of such a salt include an acid addition salt with an inorganic acid, such as hydrochloric acid, hydrobromic acid, hydroiodic acid, sulfuric acid, nitric acid, phosphoric acid, or the like; and an acid addition salt with an organic acid, such as formic acid, acetic acid, propionic acid, oxalic acid, malonic acid, succinic acid, fumaric acid, hemifumaric acid, maleic acid, lactic acid, malic acid, citric acid, tartaric acid, carbonic acid, picric acid, methanesulfonic acid, ethanesulfonic acid, glutamic acid, or the like. These salts can be prepared by conventional methods. Hemifumarate may be exemplified in an embodiment.

Compound A or a pharmaceutically acceptable salt thereof exhibits, for example, an inhibitory activity of a kinase activity of an EML4-ALK fusion protein, and is useful as an active ingredient of a pharmaceutical composition for the treatment of cancer.

The dose of compound A or a pharmaceutically acceptable salt thereof can be appropriately determined depending on individual cases taken into consideration, for example, symptoms, age of the patient, sex, or the like.

For ordinary oral administration, the daily dosage for an adult is suitably 0.001 mg/kg or more to 100 mg/kg or less, preferably 0.005 mg/kg to 30 mg/kg, and more preferably 0.01 mg/kg to 10 mg/kg. This is administered in one dose, or divided into two to four doses per day.

The content of Compound A or a pharmaceutically acceptable salt thereof is, for example, with respect to the weight of a pharmaceutical composition for oral administration, 1% by weight or more to 70% by weight or less, 5% by weight or more to 50% by weight or less in an embodiment, and 10% by weight or more to 40% by weight or less in an embodiment. The amount contained of Compound A or a pharmaceutically acceptable salt thereof is, in the whole formulation, 1 mg or more to 200 mg or less, 5 mg or more to 150 mg or less in an embodiment, and 40 mg or more to 50 mg or less in an embodiment.

The proportion of crystals of Compound A or a pharmaceutically acceptable salt thereof, which are used in the present invention, is not particularly limited, so long as it is within a range where Compound A or a pharmaceutically acceptable salt thereof is stable during storage. The proportion of the crystals can be calculated by, for example, a differential scanning calorimeter analysis (DSC analysis) method, a powder X-ray diffraction method, a solid-state NMR method, a near-infrared spectroscopy (NIR) method, or the like.

As a method of calculating the proportion of crystals of Compound A hemifumarate in Compound A hemifumarate, for example, the spectrum is measured, as a near-infrared spectroscopy measurement, by a Fourier transform near-infrared spectrometer (MPA, Bruker Optics K.K.) (measurement range; 12500 $cm^{-1}$ to 5800 $cm^{-1}$, resolution; 8 $cm^{-1}$, number of scans; 32), and the obtained spectrum is secondary-differentiated (Savitzky-Golay convolution method), and can be analyzed using a near-infrared spectrum analysis software (for example, OPUS, Bruker Optics K.K.). The pharmaceutical composition for oral administration is powdered using a mortar and pestle to measure the spectrum. Before the spectrum measurement of the pharmaceutical composition for oral administration, spectra of preparations, in which crystals of Compound A hemifumarate are mixed in various proportions, are regression-analyzed by a partial least square method to create a calibration curve, and each spectrum obtained from the pharmaceutical composition for oral administration is interpolated into the calibration curve to calculate the proportion of crystals of Compound A hemifumarate.

The proportion of the crystals is, for example, with respect to the total amount of Compound A or a pharmaceutically acceptable salt thereof, 60% or more, 60% or more to 100% or less in an embodiment, 70% or more to 100% or less in an embodiment, 80% or more to 100% or less in an embodiment, 90% or more to 100% or less in an embodiment, 60% or more to less than 100% in an embodiment, 70% or more to less than 100% in an embodiment, 80% or more to less than 100% in an embodiment, and 90% or more to less than 100% in an embodiment. In connection with this, numerical values used are interpreted as a larger variable value, in general, within an experimental error (for example, within the 95% confidence interval for the mean), or within ±10% of the indicated value, and all the values of the variable.

The pharmaceutical composition for oral administration of the present invention can further comprise a pharmaceutical additive capable of controlling a water content during a formulation step and/or storage (hereinafter sometimes referred to as a pharmaceutical additive capable of controlling a water content in a formulation). The pharmaceutical additive capable of controlling a water content in a formulation is not particularly limited, so long as the additive per se exhibits loss on drying capable of keeping the composition comprising Compound A or a pharmaceutically acceptable salt thereof stable; or a stable pharmaceutical composition for oral administration comprising Compound A or a pharmaceutically acceptable salt thereof can be provided by keeping the water content of the composition comprising Compound A or a pharmaceutically acceptable salt thereof during a formulation step (in particular, a granulation step) low, or by further reducing the water content in the formulation and maintaining the water content. Examples of the additive include sugars and/or sugar alcohols, and the additive is D-mannitol, maltose, maltitol, erythritol, xylitol, lactose (lactose hydrate), sucrose, glucose, sorbitol, trehalose, lactitol, fructose, arabinose, or trehalose in an embodiment, lactose (lactose hydrate) or D-mannitol in an embodiment, and D-mannitol in an embodiment.

The loss on drying of the pharmaceutical additive capable of controlling a water content in a formulation can be measured, for example, in a similar manner to the Loss on Drying Test, as defined in the General Tests of The Japanese Pharmacopoeia, Sixteenth Edition. In an embodiment, the loss on drying can be measured by allowing the pharmaceutical additive to stand under predetermined temperature and humidity conditions to moisturize it until the weight (mass) reaches a constant weight (mass), and then by drying it under predetermined temperature and humidity conditions until the weight (mass) reaches a constant weight (mass). In an embodiment, the loss on drying of a pharmaceutical additive, as measured by putting the pharmaceutical additive into a bottle, allowing the bottle to stand under opened conditions of 40° C. and 75% RH for 1 week, and measuring the loss on drying after storage by the loss on drying test (for example, HR73 Halogen Moisture Analyzer (manufactured by METTLER TOLEDO) is used as an apparatus, and the measurement is carried out until the weight of the sample reaches a constant weight at 80° C.) is, for example, 20% or less, 1.0% or less in an embodiment, 0.5% or less in an embodiment, and 0.4% or less in an embodiment.

The loss on drying of a pharmaceutical composition (for example, a tablet) can be measured, for example, in a similar manner to the Loss on Drying Test, as defined in the General Tests of The Japanese Pharmacopoeia, Sixteenth Edition. In an embodiment, the loss on drying can be measured by allowing the pharmaceutical composition (for example, a tablet) to stand under predetermined temperature and humidity conditions to moisturize it until the weight (mass) reaches a constant weight (mass), and then by drying it under predetermined temperature and humidity conditions until the weight (mass) reaches a constant weight (mass). In an embodiment, the loss on drying of a pharmaceutical composition (for example, a tablet), as measured by putting the pharmaceutical composition (for example, a tablet) into a bottle, allowing the bottle to stand under opened conditions of 40° C. and 75% RH for 1 week, and measuring the loss on drying after storage by the loss on drying test (for example, HR73 Halogen Moisture Analyzer (manufactured by METTLER TOLEDO) is used as an apparatus, and the measurement is carried out until the weight of the sample reaches a constant weight at 80° C.) is, for example, 4.0% or less, 3.0% or less in an embodiment, and 2.0% or less in an embodiment.

The pharmaceutical additive capable of controlling a water content in a formulation may be appropriately added alone, or as a combination of two or more, in appropriate amounts.

The content is, with respect to the total weight of the pharmaceutical composition for oral administration, for example, 20% by weight or more to 90% by weight or less, 30% by weight or more to 80% by weight or less in an embodiment, 40% by weight or more to 70% by weight or less in an embodiment, 50% by weight or more to 70% by weight or less in an embodiment, and 50% by weight or more to 60% by weight or less in an embodiment.

The pharmaceutical composition for oral administration of the present invention may be various formulations, such as tablets, capsules, powders, granules, fine granules, dry syrups, or the like. It is a tablet or a capsule in an embodiment, and a tablet in an embodiment.

In the pharmaceutical composition for oral administration of the present invention, various pharmaceutical additives, such as binders, disintegrating agents, corrigents, effervescent agents, sweeteners, flavors, lubricants, buffers, antioxidants, stabilizers, surfactants, film coating agents, and the like, may be appropriately used, if desired, to the extent that the effects of the present invention can be achieved.

Examples of the binders include gum arabic, hypromellose, hydroxypropyl cellulose, hydroxyethyl cellulose, and the like Examples of the disintegrating agents include corn starch, potato starch, carmellose calcium, carmellose sodium, low substituted hydroxypropyl cellulose, and the like.

Examples of the corrigents include citric acid, tartaric acid, malic acid, and the like.

Examples of the effervescent agents include sodium bicarbonate, and the like.

Examples of the sweeteners include saccharin sodium, glycyrrhizic acid, aspartame, stevia, thaumatin, and the like.

Examples of the flavors include lemon, lemon-lime, orange, menthol, and the like.

Examples of the lubricants include magnesium stearate, calcium stearate, and the like.

Examples of the buffers include citric acid, succinic acid, fumaric acid, tartaric acid, ascorbic acid, and salts thereof; glutamic acid, glutamine, glycine, aspartic acid, alanine, arginine, and salts thereof; magnesium oxide, zinc oxide, magnesium hydroxide, phosphoric acid, boric acid, and salts thereof; and the like.

Examples of the antioxidants include citric acid, sodium nitrite, ascorbic acid, L-ascorbic acid stearate ester, sodium hydrogen nitrite, sodium sulfite, α-thioglycerin, sodium edetate, erythorbic acid, cysteine hydrochloride, dried sodium sulfite, potassium dichloroisocyanurate, soybean lecithin, sodium thioglycolate, sodium thiomalate, natural vitamin E, tocopherol, d-δ-tocopherol, tocopherol acetate ester, mixed tocopherols concentrate, ascorbic acid palmitate, sodium pyrosulfite, butylhydroxyanisole, 1,3-butylene glycol, benzotriazole, pentaerythrityl-tetrakis[3-(3,5-di-t-butyl-4-hydroxyphenyl)propionate], 2-mercaptobenzimidazole, propyl gallate, dibutylhydroxytoluene, and the like.

The antioxidants also function as stabilizers. Examples of the stabilizers include citric acid; and citric acid hydrate, calcium citrate, sodium citrate hydrate, sodium dihydrogen citrate, disodium citrate, and the like in an embodiment.

Examples of the surfactants include poly sorbate 80, sodium lauryl sulfate, polyoxyethylene hydrogenated castor oil, and the like.

Examples of the film coating agents include hypromellose, polyvinyl alcohol, and the like.

These pharmaceutical additives may be appropriately added alone, or as a combination of two or more, in appropriate amounts. With respect to the contents of the pharmaceutical additives, each pharmaceutical additive may be used in an amount such that the desired effects of the present invention may be achieved.

The pharmaceutical composition for oral administration of the present invention can be produced by known methods comprising the steps of, for example, pulverization, mixing, granulation, drying, molding (tableting), film coating, crystallization, and the like. The method of manufacturing a pharmaceutical composition for oral administration of the present invention will be explained below.

Pulverization Step and Mixing Step

In the pulverization step, both the apparatus and the means are not particularly limited, so long as it is a method in which Compound A or a pharmaceutically acceptable salt thereof and appropriate pharmaceutical additives can be pulverized in an ordinary pharmaceutical manner. Examples of a pulverizer include a hammer mill, a ball mill, a jet mill, a colloid mill, and the like. The conditions for pulverization may be appropriately selected and are not particularly limited.

In the step of mixing components subsequent to the pulverization step, both the apparatus and the means are not particularly limited, so long as it is a method in which the components can be uniformly mixed in an ordinary pharmaceutical manner.

Granulation Step

In the granulation step, both the apparatus and the means are not particularly limited, so long as it is a method in which Compound A or a pharmaceutically acceptable salt thereof and appropriate pharmaceutical additives can be granulated in an ordinary pharmaceutical manner.

Examples of a granulation method and a granulation apparatus, which are used in a wet granulation using a solvent such as water, include a high shear granulation method, a milling (pulverization) granulation method, a fluidized bed granulation method, an extrusion granulation method, a tumbling granulation method, and a spray granulation method; and apparatuses and the like, which are used in these methods. A fluidized bed granulation method and a fluidized bed granulator are preferable, and a drying method is not particularly limited, so long as it can be dried in an ordinary pharmaceutical manner.

During granulation, it is preferable that the water content is low in order to inhibit a decrease in the proportion of crystals of Compound A or a pharmaceutically acceptable salt thereof. The water content during granulation is, for example, 30% or less, 5% or less in an embodiment, 3% or less in an embodiment, 2% or less in an embodiment, and 1% or less in an embodiment. The granulation method is not particularly limited, so long as the water content can be controlled within the range. Examples of such a granulation method include a milling (pulverization) granulation method, a fluidized bed granulation method, a tumbling granulation method, and a spray granulation method; and a fluidized bed granulation method in an embodiment.

The water content can be measured, for example, by a loss on drying method, or the like. As an apparatus, for example, a halogen moisture analyzer (METTLER TOLEDO) may be used.

A high shear granulation method can be selected, when conditions capable of reducing the water content in granules during granulation are used.

As a method not using water during granulation, a wet granulation method using a non-aqueous solvent, or a dry granulation method, can also be used.

Drying Step

In the drying step, both the apparatus and the means are not particularly limited, so long as it is a method in which the granulated product can be dried in an ordinary pharmaceutical manner. Examples of the apparatus include a forced-air dryer, a dryer under reduced pressure, a vacuum dryer, a fluidized bed granulation dryer, and the like.

After drying, the dried product may be sieved and sized using a sieve, a comil, or the like, if desired.

Molding Step

In the molding step, both the apparatus and the means are not particularly limited, so long as it is a method of molding the pharmaceutical composition for oral administration of the present invention. Examples of the method include a method in which, without the granulation and drying step, Compound A or a pharmaceutically acceptable salt thereof and appropriate pharmaceutical additives are mixed, and directly compression-molded to prepare the pharmaceutical composition for oral administration; a method in which Compound A or a pharmaceutically acceptable salt thereof and appropriate pharmaceutical additives are granulated and dried, and compression-molded to prepare the pharmaceutical composition for oral administration; a method in which Compound A or a pharmaceutically acceptable salt thereof and appropriate pharmaceutical additives are granulated, and further mixed with a lubricant, and the mixture is compression-molded to prepare the pharmaceutical composition for oral administration; and the like.

Examples of a tableting machine include a rotary tableting machine, an oil press, and the like.

The conditions for tableting, such as tableting pressure, are not particularly limited, so long as it is tableting pressure capable of compression-molding.

The hardness of the tableted product is not particularly limited, so long as it is not damaged during the manufacturing process, the distribution process, and the like. The hardness may be, for example, 40 to 200 N.

Film Coating Step

After tableting, the surface of the pharmaceutical composition for oral administration may be film coated.

The method of film coating is not particularly limited, so long as it may be coated in an ordinary pharmaceutical manner. Examples of the coating include pan coating, dip coating, and the like.

A film coating agent may be appropriately added alone, or as a combination of two or more, in appropriate amounts.

The coating rate is not particularly limited, so long as a film can be formed. The coating rate is, for example, with respect to the total weight of the pharmaceutical composition for oral administration, 1% by weight to 10% by weight, or the like.

During film coating or after film coating, the coated product may be dried. The drying method is not particularly limited, so long as it may be dried in an ordinary pharmaceutical manner. The conditions for drying are not particularly limited, so long as they are appropriately selected in view of, for example, the stability of the pharmaceutical composition for oral administration.

Crystallization Step

When the proportion of crystals of Compound A or a pharmaceutically acceptable salt thereof is reduced, a step of promoting crystallization may be adopted. Examples of the step include a microwave irradiation treatment, an ultrasonic irradiation treatment, a low frequency irradiation treatment, a thermal electron irradiation treatment, and the like.

As the microwave irradiation treatment, for example, a wavelength of 10 MHz to 25 GHz may be irradiated. Although the treatment time depends on the degree of an initial crystal proportion, or pharmaceutical additive components, it is performed, for example, for 10 seconds to 60 minutes. The irradiation may be continuous or intermittent, and at any time.

As the ultrasonic irradiation treatment, for example, sound waves with a frequency of 10 kHz to 600 kHz may be irradiated. Although the treatment time depends on the degree of a crystal proportion, or pharmaceutical additive components, it is performed, for example, for 10 seconds to 24 hours. The irradiation may be continuous or intermittent, and at any time.

The present invention includes a method of stabilizing Compound A or a pharmaceutically acceptable salt thereof by the proportion of crystals of Compound A or a pharmaceutically acceptable salt thereof, and/or by a pharmaceutical additive capable of controlling a water content in a formulation.

The present invention includes a use of a pharmaceutical additive capable of controlling a water content in a formulation, in the manufacture of a stable pharmaceutical composition for oral administration comprising Compound A or a pharmaceutically acceptable salt thereof.

With respect to "crystals of Compound A or a pharmaceutically acceptable salt thereof", "a pharmaceutical additive capable of controlling a water content in a formulation" and "Compound A or a pharmaceutically acceptable salt thereof", which are used in the stabilizing method of the present invention, and the use of a pharmaceutical additive capable of controlling a water content in a formulation of the present invention, the explanations therefor described in the pharmaceutical composition for oral administration of the present invention can be directly applied.

With respect to the content of each component, their blending method, and the like in the stabilizing method of the present invention, and the use of a pharmaceutical additive capable of controlling a water content in a formulation of the present invention, the explanations therefor described in the pharmaceutical composition for oral administration of the present invention and the method of producing the same can be directly applied.

EXAMPLES

The present invention will now be further illustrated by, but is by no means limited to, the following Comparative Examples, Examples, and Experimental Examples.

Comparative Example 1 and Examples 1 to 3

The formulations of Comparative Example 1 and Examples 1 to 3 are shown in Tables 1 and 2. Compound A hemifumarate, which was used below, had been prepared in accordance with a method described in WO 2010/128659, or in a similar fashion to that

TABLE 1

|  | Comparative Example 1 | Example 1 |
|---|---|---|
| Compound A hemifumarate | 11.05 | 44.2 |
| Lactose hydrate | 53.75 | 215.0 |
| Microcrystalline cellulose | 4.5 | 18.0 |
| Low-substituted hydroxypropyl cellulose | 9.0 | 36.0 |
| Hydroxypropyl cellulose | 1.8 | 7.2 |
| Microcrystalline cellulose | 4.5 | 18.0 |
| Low-substituted hydroxypropy cellulose | 4.5 | 18.0 |
| Magnesium stearate | 0.9 | 3.6 |
| Subtotal | 90.0 | 360.0 |
| Film-coating agent (Opadry 03F42203) | 2.7 | 10.8 |
| Total | 92.7 | 370.8 |

Unit: mg

TABLE 2

|  | Example 2 | Example 3 |
|---|---|---|
| Compound A hemifumarate | 44.2 | 44.2 |
| D-mannitol | 82.5 | 86.12 |
| Hydroxypropyl cellulose | 4.2 | 4.32 |
| Low-substituted hydroxypropyl cellulose | 7.0 | 7.2 |
| Magnesium stearate | 2.1 | 2.16 |
| Subtotal | 140.0 | 144.0 |
| Film-coating agent (Opadry 03F42203) | 4.2 | 4.3 |
| Total | 144.2 | 148.3 |

Unit: mg

Pharmatose 200M (product name, manufactured by FrieslandCampina DMV BV) was used as lactose hydrate, HPC-L (product name, manufactured by Nippon Soda Co., Ltd.) was used as hydroxypropyl cellulose, Parteck LUB MST (product name, manufactured by Merck KGaA) was used as magnesium stearate, and PEARLITOL 50C (product name, manufactured by ROQUETTE) was used as D-mannitol.

Comparative Example 1

In accordance with the formulation described in Table 1, 110.5 g of Compound A hemifumarate, 537.5 g of lactose hydrate, 45 g of microcrystalline cellulose (product name: Ceolus PH-101, manufactured by Asahi Kasei Chemicals Corporation), 90 g of low-substituted hydroxypropyl cellulose (product name: L-HPC LH-21, manufactured by Shin-Etsu Chemical Co., Ltd.), and 18 g of hydroxypropyl cellulose were mixed using a high shear granulator (product name: VG-05, manufactured by Powrex Corporation), and 300 g of purified water was further added thereto, and the mixture was granulated. The water content of the granulated product during granulation was 27%. Two additional lots of granulation were performed, and the granulated product was obtained by drying for 15 hours using a vacuum dryer (product name: DB-30, manufactured by ULVAC, Inc.). After 2403 g of the obtained granulated product was sieved, 135 g of microcrystalline cellulose (product name: Ceolus PH-102, manufactured by Asahi Kasei Chemicals Corporation), 135 g of low-substituted hydroxypropyl cellulose (product name: L-HPC LH-11, manufactured by Shin-Etsu Chemical Co., Ltd.), and 27 g of magnesium stearate were added thereto, and mixed using a mixer (product name: Container Mixer LM20, manufactured by Kotobuki Industries Co., Ltd.) to obtain a mixed product (granules for tablet compression). The obtained mixed product was formed into tablets using a rotary tableting machine (product name: HT-X20, manufactured by HATA TEKKOSHO Co., Ltd.) to obtain tablets (uncoated tablets). The obtained uncoated tablets (1350 g) were film coated using a film coating machine (product name: HCT-30, manufactured by Freund Corporation) with a liquid, prepared by dissolving/dispersing OPADRY 03F42203 (product name, manufactured by Colorcon) in purified water, so that the concentration of OPADRY 03F42203 was 10% by weight in total (concentration of solid components). An additional lot of film coating was performed, to obtain tablets (film coated tablets) of Comparative Example 1.

Example 1

In accordance with the formulation described in Table 1, 442 g of Compound A hemifumarate, 2150 g of lactose hydrate, 180 g of microcrystalline cellulose (product name: Ceolus PH-101, manufactured by Asahi Kasei Chemicals Corporation), 360 g of low-substituted hydroxypropyl cellulose (product name: L-HPC LH-21, manufactured by Shin-Etsu Chemical Co., Ltd.), and 72 g of hydroxypropyl cellulose were mixed using a high shear granulator (product name: VG-25, manufactured by Powrex Corporation), and the mixture was granulated by adding 1170 g of purified water. The water content of the granulated product during granulation was 27%. Nine additional lots of granulation were performed, and the granulated product was obtained by drying for 1 hour using a fluidized bed granulation dryer (product name: GPCG-PRO-5, manufactured by Powrex Corporation). After 32040 g of the obtained granulated product was sieved, 1800 g of microcrystalline cellulose (product name: Ceolus PH-102, manufactured by Asahi Kasei Chemicals Corporation), 1800 g of low-substituted hydroxypropyl cellulose (product name: L-HPC LH-11, manufactured by Shin-Etsu Chemical Co., Ltd.), and 360 g of magnesium stearate were added thereto, and mixed using a mixer (product name: Container Mixer PM200, manufactured by Kotobuki Industries Co., Ltd.) to obtain a mixed product (granules for tablet compression). The obtained mixed product was formed into tablets using a rotary tableting machine (product name: HT-CVX-TYPEIII20, manufactured by HATA TEKKOSHO Co., Ltd.) to obtain tablets (uncoated tablets). The obtained uncoated tablets (36000 g) were film coated using a film coating machine (product name: PRC-20/60, manufactured by Powrex Corporation) with a liquid, prepared by dissolving/dispersing OPADRY 03F42203 (product name, manufactured by Colorcon) in purified water, so that the concentration of OPADRY 03F42203 was 10% by weight in total (concentration of solid components), to obtain tablets (film coated tablets) of Example 1.

Example 2

In accordance with the formulation described in Table 2, 6630 g of Compound A hemifumarate and 12375 g of D-mannitol were mixed using a fluidized bed granulation dryer (product name: GPCG-PRO-15, manufactured by Powrex Corporation). After mixing, the mixture was granulated by spraying 9000 g of a hydroxypropyl cellulose aqueous solution (solid content: 7% by weight) as a binder, and dried to obtain a granulated product. The water content of the granulated product during granulation was 0.43% at the maximum. After 19635 g of the obtained granulated product was sieved, 1050 g of low-substituted hydroxypropyl cellulose (product name: L-HPC LH-21, manufactured by Shin-Etsu Chemical Co., Ltd.) and 315 g of magnesium stearate were added thereto, and mixed using a mixer (product name: Container Mixer PM200, manufactured by Kotobuki Industries Co., Ltd.) to obtain a mixed product (granules for tablet compression). The obtained mixed product was formed into tablets using a rotary tableting machine (product name: HT-CVX-TYPEIII20, manufactured by HATA TEKKOSHO Co., Ltd.) to obtain tablets (uncoated tablets). The obtained uncoated tablets (21000 g) were film coated using a film coating machine (product name: PRC-20/60, manufactured by Powrex Corporation) with a liquid, prepared by dissolving/dispersing OPADRY 03F42203 (product name, manufactured by Colorcon) in purified water, so that the concentration of OPADRY 03F42203 was 10% by weight in total (concentration of solid components), to obtain tablets (film coated tablets) of Example 2.

Example 3

Tablets (film coated tablets) of Example 3 were prepared in a similar manner to that of Example 2, in accordance with the formulation described in Table 2.

Experimental Example 1

Calculation of Proportion of Crystals

With respect to the tablets (film coated tablets) prepared in Comparative Example 1, Example 1, Example 2, and Example 3, the proportion of crystals of Compound A hemifumarate after production was calculated by near-infrared spectroscopy.

More particularly, the spectrum was measured by a Fourier transform near-infrared spectrometer (product name: MPA, Bruker Optics K.K.) (measurement range; 12500 $cm^{-1}$ to 5800 $cm^{-1}$, resolution; 8 $cm^{-1}$, number of scans; 32), and the obtained spectrum was secondary-differentiated (Savitzky-Golay convolution method), and analyzed using a near-infrared spectrum analysis software (product name: OPUS, Bruker Optics K.K.). The tablets were powdered using a mortar and pestle, and the spectra were measured. Before the spectrum measurement of the tablets, spectra of preparations, in which crystals of Compound A hemifumarate were mixed in various proportions, were regression-analyzed by a partial least square method to create a calibration curve, and each spectrum obtained from the tablets was interpolated into the calibration curve to calculate the proportion of crystals of Compound A hemifumarate. The results are shown in Table 4.

Experimental Example 2

Measurement of Related Substances

The tablets (film coated tablets) prepared in Comparative Example 1, Example 1, Example 2, and Example 3 were put into bottles, and allowed to stand under opened conditions of 40° C. and 75% RH for 1 month and 3 months. Related substances after storage were measured by an HPLC method. The measurement of related substances was carried out under the following conditions:

As an HPLC column, Kinetex XB-C18, particle size: 2.6 µm, 4.6 mm (inner diameter)×75 mm (manufactured by Phenomenex Inc.), or its equivalent, was used, and maintained at 40° C.

As mobile phase A, a perchlorate solution (pH 2.2) was used, and as mobile phase B, acetonitrile was used.

As sample solutions, samples were diluted with a perchlorate solution (pH 2.2)/acetonitrile mixture (=4/1) was used, so that the concentration of compound A was 0.8 mg/mL.

As a standard solution, a standard was diluted with a perchlorate solution (pH 2.2)/acetonitrile mixture (=4/1) was used, so that the concentration of compound A was 0.008 mg/mL.

The measurement of related substances was carried out using an ultraviolet absorption spectrophotometer (wavelength: 220 nm), in accordance with the gradient program shown in Table 3 below, and the percentage of each related substance was calculated based on the ratio of the peak area of each related substance to the peak area of the standard solution.

The measurement results of a related substance having a relative retention time of about 1.06 with respect to the peak of Compound A are shown in Table 4.

TABLE 3

| Time (min.) | Mobile phase A (%) | Mobile phase B (%) |
|---|---|---|
| 0→2 | 96 | 4 |
| 2→5 | 96→85 | 4→15 |
| 5→20 | 85→68 | 15→32 |
| 20→25 | 68→30 | 32→70 |
| 25→26 | 30 | 70 |
| 26→26.1 | 30→96 | 70→4 |
| 26.1→30 | 96 | 4 |

TABLE 4

| | Proportion of crystals (%) | Related substance (%) Opened conditions of 40° C. and 75% RH | | |
|---|---|---|---|---|
| | | At the beginning of test | 1 month | 3 months |
| Comparative Example 1 | 26 | 0.05 | 0.21 | N.T. |
| Example 1 | 64 | <LOQ | 0.11 | 0.26 |
| Example 2 | 98 | <LOQ | <LOQ | N.T. |
| Example 3 | 85 | <LOQ | <LOQ | <LOQ |

LOQ: Limit of Quantitation,
N.T.: Not Tested

Comparative Example 1 was prepared by a high shear granulation method, as similar to Example 1, but they were different from each other in the proportion of crystals. It is inferred that this is due to the difference in drying time caused by different drying methods.

In the tablet of Example 1, in which the proportion of crystals of Compound A hemifumarate was 64%, the percentage of the related substance was 0.11% after storage under opened conditions of 40° C. and 75% RH for 1 month, and the percentage of the related substance was 0.26% after storage for 3 months. In the tablets of Examples 2 and 3, the percentage of the related substance after storage for 1 month was less than the limit of quantitation (LOQ). The tablets of these Examples contained a small amount of a related substance, in comparison with the tablet of the Comparative Example, and were stable. For reference, the LOQ is 0.05%.

As described above, it was confirmed that when the proportion of crystals of Compound A hemifumarate increased, the generation of related substances could be inhibited.

Examples 4 to 15

After water was added to the crystals of Compound A hemifumarate, it was dried to obtain Compound A hemifumarate, of which the proportion of crystals was 62%. Various pharmaceutical additives shown in Table 5 were physically mixed with the obtained Compound A hemifumarate at a weight ratio of 1:1, and the obtained pharmaceutical compositions were put into bottles and allowed to stand under opened conditions of 40° C. and 75% RH for 1 month and 3 months.

Experimental Example 3

Measurement of Related Substances

Related substances contained in the pharmaceutical compositions of the Examples were measured in a similar manner to that of Experimental Example 2. The measurement results of a related substance having a relative retention time of about 1.06 with respect to the peak of Compound A are shown in Table 5.

Experimental Example 4

Measurement of Loss on Drying of Pharmaceutical Additives

The measurement of loss on drying of various pharmaceutical additives shown in Table 5 was carried out in a similar manner to the test for above loss on drying. The pharmaceutical additives used were lactose hydrate (product name: Pharmatose 200M, manufactured by FrieslandCampina DMV BV), hydroxypropyl cellulose (product name: HPC-L, manufactured by Nippon Soda Co., Ltd.), magnesium stearate (product name: Parteck LUB MST, manufactured by Merck KGaA), D-mannitol (product name: PEARLITOL 50C, manufactured by ROQUETTE), microcrystalline cellulose (product name: Ceolus PH-101, manufactured by Asahi Kasei Chemicals Corporation), anhydrous dibasic calcium phosphate (product name: GS, manufactured by Kyowa Chemical Industry Co., Ltd.), hypromellose (product name: TC-5E, Shin-Etsu Chemical Co., Ltd.), corn starch (product name: corn starch, manufactured by Nihon ShokuhinKako Co., Ltd.), low-substituted hydroxypropyl cellulose (product name: L-HPC LH-21, low-substituted hydroxypropyl cellulose), croscarmellose sodium (product name: KICCOLATE ND-2HS, manufactured by Nichirin Chemical Industries, Ltd.), calcium stearate (product name: Parteck LUB CST, manufactured by Merck KGaA), and talc (product name: Hi-filler, manufactured by Matsumura Sangyo Co., Ltd.).

TABLE 5

| Number of Example | Pharmaceutical additive | Loss on drying of pharmaceutical additive (%) | 40° C. · 75% RH 1 month Amount of related substance after storage (%) | 40° C. · 75% RH 3 months Amount of related substance after storage (%) |
|---|---|---|---|---|
| Reference value | (Not added) | — | <LOQ | 0.06 |
| Example 4 | anhydrous dibasic calcium phosphate | 0.20 | <LOQ | 0.06 |
| Example 5 | Lactose hydrate | 0.26 | <LOQ | <LOQ |
| Example 6 | D-mannitol | 0.32 | <LOQ | <LOQ |
| Example 7 | Talc | 0.46 | <LOQ | 0.06 |
| Example 8 | Calcium stearate | 0.53 | <LOQ | 0.06 |
| Example 9 | Magnesium stearate | 1.5 | <LOQ | 0.09 |
| Example 10 | Microcrystalline cellulose | 7.8 | 0.06 | 0.10 |
| Example 11 | Hydroxypropyl cellulose | 9.3 | 0.05 | 0.11 |
| Example 12 | Hypromellose | 9.5 | <LOQ | 0.09 |
| Example 13 | Corn starch | 13.2 | 0.06 | 0.11 |
| Example 14 | Low-substituted Hydroxypropyl cellulose | 13.4 | 0.05 | 0.11 |

TABLE 5-continued

| Number of Example | Pharmaceutical additive | Loss on drying of pharmaceutical additive (%) | 40° C. · 75% RH 1 month Amount of related substance after storage (%) | 40° C. · 75% RH 3 months Amount of related substance after storage (%) |
|---|---|---|---|---|
| Example 15 | Croscarmellose sodium | 18.6 | 0.05 | 0.10 |

LOQ: Limit of Quantitation

It was confirmed that the pharmaceutical compositions of Examples 4 to 15 were stable after 1 month and 3 months under opened conditions of 40° C. and 75% RH, and that when the proportion of crystals of Compound A hemifumarate increased, the generation of related substances could be inhibited. It was suggested that, in particular, lactose hydrate (Example 5) and D-mannitol (Example 6) were suitable from the viewpoint of inhibition of the generation of related substances.

Experimental Example 5

Measurement of Loss on Drying of Tablets of Examples 2 and 3

The loss on drying of the tablets of Examples 2 and 3 after storage under opened conditions of 40° C. and 75% RH for 1 week was measured in a similar manner to that of Experimental Example 4. The results are shown in Table 6. The loss on drying in the tablets, which contained D-mannitol in the formulations, was low.

TABLE 6

| | Loss on drying (%) |
|---|---|
| Example 2 | 1.3 |
| Example 3 | 1.4 |

From the above results, a stable formulation comprising Compound A or a pharmaceutically acceptable salt thereof can be provided by controlling the proportion of crystals of Compound A or a pharmaceutically acceptable salt thereof, and/or by using a pharmaceutical additive capable of controlling a water content in a formulation.

INDUSTRIAL APPLICABILITY

According to the present invention, a stable pharmaceutical composition for oral administration comprising Compound A or a pharmaceutically acceptable salt thereof, wherein the generation of related substances during storage, is inhibited.

Although the present invention has been described with reference to specific embodiments, various changes and modifications obvious to those skilled in the art are possible without departing from the scope of the appended claims.

The invention claimed is:

1. A pharmaceutical composition for oral administration comprising:
6-ethyl-3-({3-methoxy-4-[4-(4-methylpiperazin-1-yl)piperidin-1-yl]phenyl}amino)-5-(tetrahydro-2H-pyran-4-ylamino)pyrazine-2-carboxamide or a pharmaceutically acceptable salt thereof and at least one pharmaceutical additive selected from the group consisting of lactose, D-mannitol, anhydrous dibasic calcium phosphate, talc, calcium stearate, magnesium stearate, microcrystalline cellulose, hydroxypropyl cellulose, hypromellose, corn starch, low-substituted hydroxypropyl cellulose, and croscarmellose sodium, wherein a proportion of crystals of 6-ethyl-3-({3-methoxy-4-[4-(4-methylpiperazin-1-yl)piperidin-1-yl]phenyl}amino)-5-(tetrahydro-2H-pyran-4-ylamino)pyrazine-2-carboxamide or the pharmaceutically acceptable salt thereof is at least 62% with respect to a total amount of 6-ethyl-3-({3-methoxy-4-[4-(4-methylpiperazin-1-yl)piperidin-1-yl]phenyl}amino)-5-(tetrahydro-2H-pyran-4-ylamino)pyrazine-2-carboxamide or the pharmaceutically acceptable salt thereof in the pharmaceutical composition, wherein the pharmaceutical composition exhibits an increase of no more than 0.11% of an oxidative decomposition product having a relative retention time of 1.06 with respect to a retention time of 6-ethyl-3-({3-methoxy-4-[4-(4-methylpiperazin-1-yl)piperidin-1-yl]phenyl}amino)-5-(tetrahydro-2H-pyran-4-ylamino)pyrazine-2-carboxamide, as measured by a high-performance liquid chromatography method, after storage under opened conditions of 40° C. and 75% relative humidity for 1 month, and wherein the high-performance liquid chromatography method is performed under following conditions:
a Kinetex XB-C18 column, particle size: 2.6 μm, 4.6 mm (an inner diameter)×75 mm;
a column temperature maintained at 40° C.;
a mobile phase A of a perchlorate solution (pH 2.2);
a mobile phase B of an acetonitrile solution;
a sample solution having a sample concentration of 0.8 mg/ml of 6-ethyl-3-({3-methoxy-4-[4-(4-methylpiperazin-1-yl)piperidin-1-yl]phenyl}amino)-5-(tetrahydro-2H-pyran-4-ylamino)pyrazine-2-carboxamide in a 4:1 mixture of the perchlorate solution (pH 2.2) and the acetonitrile solution;
a standard solution having a standard solution concentration of 0.008 mg/ml of 6-ethyl-3-({3-methoxy-4-[4-(4-methylpiperazin-1-yl)piperidin-1-yl]phenyl}amino)-5-(tetrahydro-2H-pyran-4-ylamino)pyrazine-2-carboxamide in a 4:1 mixture of the perchlorate solution (pH 2.2) and the acetonitrile solution;
an ultraviolet absorption spectrophotometer detector with a wavelength at 220 nm; and
a gradient of the mobile phase A and mobile phase B is as follows:
(a) from 0 minutes to 2 minutes since sample injection, 96% mobile phase A and 4% mobile phase B;
(b) from 2 minutes to 5 minutes since sample injection, 96% incrementing down to 85% mobile phase A and 4% incrementing up to 15% mobile phase B;
(c) from 5 minutes to 20 minutes since sample injection, 85% incrementing down to 68% mobile phase A and 15% incrementing up to 32% mobile phase B;
(d) from 20 minutes to 25 minutes since sample injection, 68% incrementing down to 30% mobile phase A and 32% incrementing up to 70% mobile phase B;
(e) from 25 minutes to 26 minutes since sample injection, 30% mobile phase A and 70% mobile phase B;
(f) from 26 minutes to 26.1 minutes since sample injection, 30% incrementing up to 96% mobile phase A and 70% incrementing down to 4% mobile phase B; and (g) from 26.1 minutes to 30 minutes since sample injection, 96% mobile phase A and 4% mobile phase B.

2. The pharmaceutical composition according to claim 1, wherein the at least one pharmaceutical additive exhibits a loss on drying of 1.0% or less after storage under opened conditions of 40° C. and 75% relative humidity for 1 week.

3. The pharmaceutical composition according to claim 1, comprising 6-ethyl-3-({3-methoxy-4-[4-(4-methylpiperazin-1-yl)piperidin-1-yl]phenyl}amino)-5-(tetrahydro-2H-pyran-4-ylamino)pyrazine-2-carboxamide hemifumarate.

4. The pharmaceutical composition according to claim 1, wherein a content of 6-ethyl-3-({3-methoxy-4-[4-(4-methylpiperazin-1-yl)piperidin-1-yl]phenyl}amino)-5-(tetrahydro-2H-pyran-4-ylamino)pyrazine-2-carboxamide or the pharmaceutically acceptable salt thereof in the pharmaceutical composition is 10% by weight to 40% by weight with respect to 100% by weight of the pharmaceutical composition.

5. The pharmaceutical composition according to claim 1, wherein a pharmaceutical additive content in the pharmaceutical composition is 50% by weight to 70% by weight with respect to 100% by weight of the pharmaceutical composition.

6. The pharmaceutical composition according to claim 1, wherein a pharmaceutical additive content in the pharmaceutical composition is 50% by weight to 60% by weight with respect to 100% by weight of the pharmaceutical composition.

7. The pharmaceutical composition according to claim 1, wherein a pharmaceutical additive weight content in the pharmaceutical composition is 1.5 times to 4.5 times that of 6-ethyl-3-({3-methoxy-4-[4-(4-methylpiperazin-1-yl)piperidin-1-yl]phenyl}amino)-5-(tetrahydro-2H-pyran-4-ylamino)pyrazine-2-carboxamide or the pharmaceutically acceptable salt thereof.

8. The pharmaceutical composition according to claim 1, wherein the at least one pharmaceutical additive is lactose or D-mannitol.

9. The pharmaceutical composition according to claim 3, wherein the proportion of crystals of 6-ethyl-3-({3-methoxy-4-[4-(4-methylpiperazin-1-yl)piperidin-1-yl]phenyl}amino)-5-(tetrahydro-2H-pyran-4-ylamino)pyrazine-2-carboxamide hemifumarate is 62% to 98% with respect to the total amount of 6-ethyl-3-({3-methoxy-4-[4-(4-methylpiperazin-1-yl)piperidin-1-yl]phenyl}amino)-5-(tetrahydro-2H-pyran-4-ylamino)pyrazine-2-carboxamide hemifumarate in the pharmaceutical composition.

10. The pharmaceutical composition according to claim 9, wherein the at least one pharmaceutical additive exhibits a loss on drying of 1.0% or less after storage under opened conditions of 40° C. and 75% relative humidity for 1 week.

11. The pharmaceutical composition according to claim 9, comprising 40 mg to 50 mg of 6-ethyl-3-({3-methoxy-4-[4-(4-methylpiperazin-1-yl)piperidin-1-yl]phenyl}amino)-5-(tetrahydro-2H-pyran-4-ylamino)pyrazine-2-carboxamide hemifumarate.

12. The pharmaceutical composition according to claim 9, wherein a pharmaceutical additive content in the pharmaceutical composition is 50% by weight 70% by weight with respect to 100% by weight of the pharmaceutical composition.

13. The pharmaceutical composition according to claim 9, wherein a pharmaceutical additive content in the pharmaceutical composition is 50% by weight to 60% by weight with respect to 100% by weight of the pharmaceutical composition.

14. The pharmaceutical composition according to claim 2, wherein a pharmaceutical additive weight content in the pharmaceutical composition is 1.5 times to 4.5 times that of 6-ethyl-3-({3-methoxy-4-[4-(4-methylpiperazin-1-yl)piperidin-1-yl]phenyl}amino)-5-(tetrahydro-2H-pyran-4-ylamino)pyrazine-2-carboxamide hemifumarate.

15. The pharmaceutical composition according to claim 9, wherein the at least one pharmaceutical additive is lactose or D-mannitol.

16. The pharmaceutical composition according to claim 1, which is a tablet.

17. The pharmaceutical composition according to claim 3, which is a tablet.

18. The pharmaceutical composition according to claim 11, which is a tablet.

* * * * *